(12) United States Patent
Hoshino et al.

(10) Patent No.: US 11,166,795 B2
(45) Date of Patent: Nov. 9, 2021

(54) METHOD FOR PRODUCING DENTAL PROSTHESIS, METHOD FOR PRODUCING LITHIUM DISILICATE BLANK FOR DENTAL PROSTHESIS AND LITHIUM DISILICATE BLANK FOR DENTAL PROSTHESIS

(71) Applicant: GC CORPORATION, Tokyo (JP)

(72) Inventors: Tomohiro Hoshino, Tokyo (JP); Go Mashio, Tokyo (JP); Tatsuya Fujimoto, Tokyo (JP); Masatoshi Yoshinaga, Tokyo (JP); Hayato Yokohara, Tokyo (JP); Daisuke Ohta, Tokyo (JP)

(73) Assignee: GC CORPORATION, Tokyo (JP)

( * ) Notice: Subject to any disclaimer, the term of this patent is extended or adjusted under 35 U.S.C. 154(b) by 0 days.

(21) Appl. No.: 16/506,589

(22) Filed: Jul. 9, 2019

(65) Prior Publication Data
US 2019/0328495 A1    Oct. 31, 2019

Related U.S. Application Data

(60) Continuation-in-part of application No. 15/499,252, filed on Apr. 27, 2017, now Pat. No. 10,405,953.
(Continued)

(30) Foreign Application Priority Data

Aug. 27, 2014    (JP) .................................. 2014-172684

(51) Int. Cl.
*C03C 10/00*    (2006.01)
*A61C 13/00*    (2006.01)
(Continued)

(52) U.S. Cl.
CPC ...... *A61C 13/0022* (2013.01); *A61C 13/0006* (2013.01); *A61C 13/083* (2013.01);
(Continued)

(58) Field of Classification Search
CPC ..................... C03C 10/0009; C03C 10/0027
See application file for complete search history.

(56) References Cited

U.S. PATENT DOCUMENTS 6,455,451 B1 *  9/2002  Brodkin .................. A61K 6/78
                                                                501/5
6,495,072 B1   12/2002  Van der Zel
(Continued)

FOREIGN PATENT DOCUMENTS

CA      2892284 A1    6/2014
CA      2880280 A1   10/2014
(Continued)

OTHER PUBLICATIONS

USPTO NFOA dated Aug. 25, 2016 in connection with U.S. Appl. No. 14/892,078.
(Continued)

*Primary Examiner* — Noah S Wiese

(57) ABSTRACT

Provided is a block body that makes it possible to quickly produce a dental prosthesis with a good accuracy. A material of the block body including $SiO_2$ in an amount of 60.0 mass % to 80.0 mass %, $Li_2O$ in an amount of 10.0 mass % to 20.0 mass %, $Al_2O_3$ in an amount of 5.1 mass % to 10.0 mass %, wherein the block body is formed in a column, and a main crystalline phase of the block body is lithium disilicate.

11 Claims, 2 Drawing Sheets

Related U.S. Application Data which is a division of application No. 14/892,078, filed as application No. PCT/JP2015/069695 on Jul. 8, 2015, now Pat. No. 9,700,392.

(51) Int. Cl.

| | | |
|---|---|---|
| *C03C 4/00* | (2006.01) | |
| *A61Q 11/00* | (2006.01) | |
| *A61C 13/083* | (2006.01) | |
| *A61K 6/831* | (2020.01) | |
| *A61K 6/833* | (2020.01) | |
| *A61K 6/853* | (2020.01) | |

(52) U.S. Cl.
CPC ............. *A61K 6/831* (2020.01); *A61K 6/833* (2020.01); *A61K 6/853* (2020.01); *A61Q 11/00* (2013.01); *C03C 4/0021* (2013.01); *C03C 10/0027* (2013.01); *C03C 2204/00* (2013.01)

(56) References Cited

U.S. PATENT DOCUMENTS

| | | | |
|---|---|---|---|
| 6,802,894 B2* | 10/2004 | Brodkin | A61K 6/17 |
| | | | 106/35 |
| 8,592,330 B2 | 11/2013 | Johannes et al. | |
| 9,321,674 B2 | 4/2016 | Ritzberger et al. | |
| 9,700,392 B2 | 7/2017 | Hoshino et al. | |
| 10,405,953 B2 | 9/2019 | Hoshino et al. | |
| 2002/0157570 A1 | 10/2002 | Brodkin et al. | |
| 2003/0073563 A1 | 4/2003 | Brodkin et al. | |
| 2005/0098064 A1 | 5/2005 | Schweiger et al. | |
| 2005/0127544 A1 | 6/2005 | Brodkin et al. | |
| 2008/0120994 A1 | 5/2008 | Schweiger et al. | |
| 2008/0248316 A1† | 10/2008 | Goto | |
| 2011/0030423 A1 | 2/2011 | Johannes et al. | |
| 2011/0257000 A1 | 10/2011 | Ritzberger et al. | |
| 2012/0241991 A1 | 9/2012 | Ritzberger et al. | |
| 2014/0148323 A1 | 5/2014 | Brown et al. | |
| 2014/0200129 A1 | 7/2014 | Durschang et al. | |
| 2014/0370464 A1 | 12/2014 | Kounga et al. | |
| 2015/0140274 A1* | 5/2015 | Burke | C03C 3/085 |
| | | | 428/156 |
| 2015/0183681 A1 | 7/2015 | Johannes et al. | |
| 2016/0287361 A1 | 10/2016 | Hoshino et al. | |
| 2018/0133113 A1 | 5/2018 | Hoshino et al. | |

FOREIGN PATENT DOCUMENTS

| | | |
|---|---|---|
| CA | 2880800 A1 | 10/2014 |
| CN | 103930086 A | 7/2014 |
| EP | 3011929 A1 | 4/2016 |
| JP | 2000313674 A | 11/2000 |
| JP | 2008515549 A | 5/2008 |
| JP | 2010-519986 A | 6/2010 |
| JP | 2010519986 A | 6/2010 |
| JP | 4777625 B2 | 9/2011 |
| JP | 2011-225441 A | 11/2011 |
| JP | 2012-223552 A | 11/2012 |
| JP | 2013-515659 A | 5/2013 |
| JP | 2014520061 A | 8/2014 |
| JP | WO2016031399 A1 | 4/2017 |
| JP | 2017128581 A | 7/2017 |
| JP | 6347792 B2 | 6/2018 |
| JP | 6633068 B2 | 1/2020 |
| KR | 20140075776 A | 6/2014 |
| WO | 2006/042046 A2 | 4/2006 |
| WO | 2008/106958 A2 | 9/2008 |
| WO | 2011/076422 A1 | 6/2011 |
| WO | 2012/021201 A1 | 7/2012 |
| WO | 2012/091201 A1 | 7/2012 |
| WO | 2012091201 A1 † | 7/2012 |
| WO | 2012/175450 A1 | 12/2012 |
| WO | 2013/053863 A2 | 4/2013 |
| WO | 2013/167723 A1 | 11/2013 |
| WO | 2014/082969 A1 | 6/2014 |
| WO | 2014082969 A1 † | 6/2014 |
| WO | 2015/034860 A1 | 3/2015 |
| WO | 2015034860 A1 † | 3/2015 |
| WO | 2016/031399 A1 | 3/2016 |

OTHER PUBLICATIONS

USPTO FOA dated Jan. 27, 2017 in connection with U.S. Appl. No. 14/892,078.
USPTO NFOA dated Dec. 20, 2018 in connection with U.S. Appl. No. 15/499,252.
USPTO NOA dated May 15, 2018 in connection with U.S. Appl. No. 15/499,252.
USPTO NOA dated Apr. 9, 2019 in connection with U.S. Appl. No. 15/499,252.
USPTO NOA dated Jul. 17, 2019 in connection with U.S. Appl. No. 15/499,252.
USPTO NFOA dated Jun. 11, 2020 in connection with U.S. Appl. No. 15/574,631.
USPTO AA dated Apr. 21, 2017 in connection with U.S. Appl. No. 14/892,078.
USPTO NOA dated May 12, 2017 in connection with U.S. Appl. No. 14/892,078.
USPTO NFOA dated Nov. 16, 2017 in connection with U.S. Appl. No. 15/499,252.
USPTO FOA dated Mar. 19, 2021 in connection with U.S. Appl. No. 15/574,631.

\* cited by examiner
† cited by third party

METHOD FOR PRODUCING DENTAL PROSTHESIS, METHOD FOR PRODUCING LITHIUM DISILICATE BLANK FOR DENTAL PROSTHESIS AND LITHIUM DISILICATE BLANK FOR DENTAL PROSTHESIS

TECHNICAL FIELD

The present invention relates to a method for producing a dental prosthesis, a method for producing a lithium disilicate blank for a dental prosthesis, and a lithium disilicate blank for a dental prosthesis.

BACKGROUND ART OF THE INVENTION

With the recent development of CAD and CAM, a dental prosthesis is produced by machining such as cutting and grinding. In producing a dental prosthesis, data of the shape of the dental prosthesis is used. The data is converted into a predetermined form to be sent to a processing apparatus, and the processing apparatus automatically carries out machining on the basis of the data, to produce the dental prosthesis. This makes it possible to quickly provide a dental prosthesis.

A dental prosthesis needs to have strength, hardness, chemical durability against the intraoral environment, and aesthetics (color and texture) similar to a natural tooth, which are basic functions as a dental prosthesis.

In addition, a dental prosthesis has complicated concavities and convexities on its occlusal surface for example, and it is also important to machine this complicated shape in a short time, without causing defects such as chippings. With a material which can be processed in a short time, a dental prosthesis can be produced more quickly.

Patent Literature 1 discloses a material for a dental prosthesis including predetermined components, with which the basic functions described above and cutting property are tried to be improved.

CITATION LIST

Patent Literatures

Patent Literature 1: JP 4777625 B

SUMMARY OF THE INVENTION

Technical Problem

However, in the invention described in Patent Literature 1, the material is machined in a state having lithium metasilicate which has an excellent cutting property as its main crystalline phase, thereafter heated to obtain lithium disilicate which is hard. In this case, a heating treatment is required after machining, therefore the material deforms even to a slight extent.

On the other hand, a material whose main crystalline phase is lithium disilicate has poor machinability. Therefore, such a material is not machined in practice. If such a material is tried to be machined, the material is difficult to be quickly machined with lithium disilicate as the main crystalline phase, therefore conditions do not match the actual production.

Considering the above problems, an object of the present invention is to provide a block body that makes it possible to quickly produce a dental prosthesis with a good accuracy.

Solution to Problem

Hereinafter the present invention will be described.

The invention of claim 1 is a block body before a dental prosthesis is produced therefrom by cutting work, the block body including a material including $SiO_2$ in an amount of 60.0 mass % to 80.0 mass %, $Li_2O$ in an amount of 10.0 mass % to 20.0 mass %, and $Al_2O_3$ in an amount of 5.1 mass % to 10.0 mass %, wherein the block body is formed in a column, and a main crystalline phase is lithium disilicate.

Here, the term "main crystalline phase" refers to a crystalline phase having the largest ratio of crystal precipitation, as a result of a high-accuracy quantitative analysis by Rietveld method of a measurement by means of a multipurpose X-ray diffractometer Empyrean (PANalytical). Hereinafter the same is applied.

The term "glass blank" refers to a blank (material) made by cooling to solidify a molten material, in which lithium disilicate as main crystalline phase is not formed yet. In contrast, the term "lithium disilicate blank" refers to a blank (material), in which lithium disilicate as main crystalline phase is formed.

The invention of claim 2 is a block body according to claim 1, wherein the material further includes at least one selected from the group consisting of $Na_2O$ in an amount of no more than 2.8 mass %, $K_2O$ in an amount of no more than 2.7 mass %, and $TiO_2$ in an amount of no more than 10.0 mass %.

The invention of claim 3 is also a block body according to claim 1, wherein the material further includes at least one selected from the group consisting of $CaO$ in an amount of no more than 3.0 mass %, $SrO$ in an amount of no more than 10.0 mass %, $BaO$ in an amount of no more than 10.0 mass %, $MgO$ in an amount of no more than 3.0 mass %, $Rb_2O$ in an amount of no more than 2.8 mass %, $Cs_2O$ in an amount of no more than 2.8 mass %, $Fr_2O$ in an amount of no more than 2.8 mass %, $BeO$ in an amount of no more than 3.0 mass %, and $RaO$ in an amount of no more than 10.0 mass %.

The invention of claim 4 is also a block body according to claim 1, wherein the material further includes $ZrO_2$ in an amount of no more than 10 mass %.

The invention of claim 5 is a block body according to claim 1, wherein machinability is the same as or better than those of first and second references, the machinability being compared in a processing time, a degree of tool wear, and chippings, the first reference being a material whose main crystalline phase is lithium metasilicate, the material including $SiO_2$ in an amount of 72.3 mass %, $Li_2O$ in an amount of 15.0 mass %, $Al_2O_3$ in an amount of 1.6 mass %, the second reference being a material including a crystalline phase of lithium metasilicate and a crystalline phase of lithium disilicate with a same ratio, $Si_2O$ in an amount of 56.3 mass %, $Li_2O$ in an amount of 14.7 mass %, and $Al_2O_3$ in an amount of 2.1 mass %.

The invention of claim 6 is a block body according to claim 1, wherein in an observation range of 60 μm in length and 60 μm in width on a cross section of the block body, an area occupied by voids is less than 2%.

The invention of claim 7 is a block body according to claim 1, wherein particles of a colorant are not observed within an observation range of 1 mm in length and 1 mm in width on a cross section of the block body.

The invention of claim 8 is a lithium disilicate blank for a dental prosthesis to be machined into a shape of a dental prosthesis without press molding, the lithium disilicate blank including $SiO_2$ in an amount of 60.0 mass % to 80.0 mass %; $Li_2O$ in an amount of 10.0 mass % to 20.0 mass %; and $Al_2O_3$ in an amount of 5.1 mass % to 10.0 mass %; wherein amain crystalline phase is lithium disilicate.

The invention of claim 9 is the lithium disilicate blank according to claim 8, wherein the lithium disilicate blank further includes at least one of $ZrO_2$ in an amount of 0.1 mass % to 10.0 mass %, and $K_2O$ in an amount of 0.2 mass % to 10 mass %.

The invention of claim 10 is a lithium disilicate blank for a dental prosthesis to be machined into a shape of a dental prosthesis to form a dental prosthesis without a heating treatment after the machining, the lithium disilicate blank including $SiO_2$ in an amount of 60.0 mass % to 80.0 mass %; $Li_2O$ in an amount of 10.0 mass % to 20.0 mass %; and $Al_2O_3$ in an amount of 5.1 mass % to 10.0 mass %, wherein a main crystalline phase is lithium disilicate.

The invention of claim 11 is the lithium disilicate blank according to claim 10, wherein the lithium disilicate blank further includes at least one of $ZrO_2$ in an amount of 0.1 mass % to 10.0 mass %, and $K_2O$ in an amount of 0.2 mass % to 10 mass %.

Advantageous Effect of Invention

According to the present invention, it is possible to obtain a dental prosthesis by machining a lithium disilicate blank as it is. Therefore, it is possible to quickly provide a dental prosthesis having high strength with a good accuracy.

DESCRIPTION OF EMBODIMENTS

A lithium disilicate blank for a dental prosthesis according to one embodiment is a block material formed in a column, such as a rectangular column and a cylinder. A dental prosthesis can be produced by deforming or grinding the block material by machining such as cutting.

Figure 1:
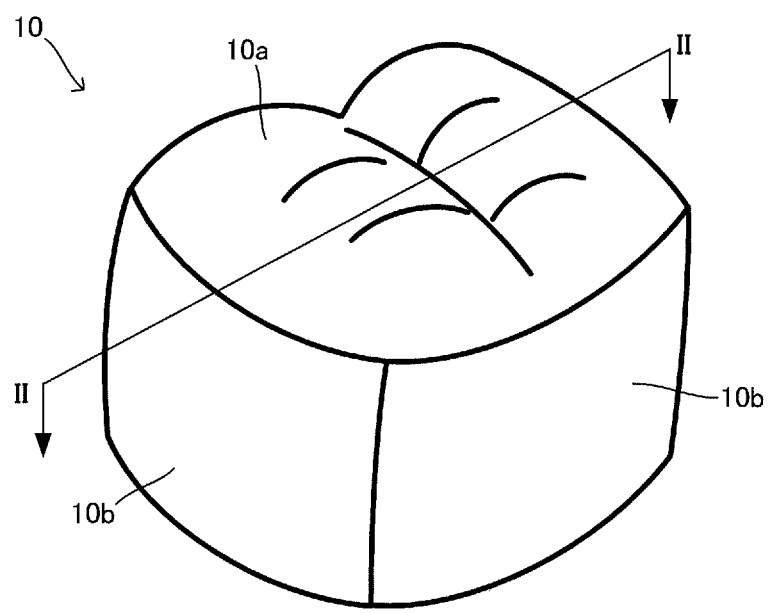
FIG. 1 is a perspective view of an external appearance of a dental prosthesis 10.
Figure 2:
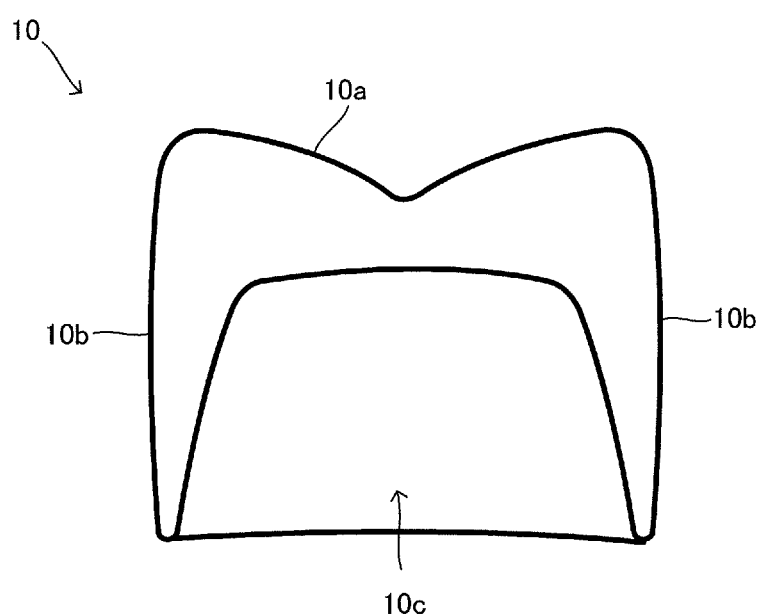
FIG. 2 is a cross-sectional view of the dental prosthesis 10.

FIGS. 1 and 2 show a dental prosthesis 10 of one example. FIG. 1 is a perspective view of an external appearance of the dental prosthesis 10. FIG. 2 shows a cross-sectional view of the dental prosthesis 10 cut along the II-II line shown in FIG. 1 in a direction of the arrows. As can be seen from FIGS. 1 and 2, the dental prosthesis 10 of the example is a tooth crown. A surface 10a on the oral cavity side and a side surface 10b are shaped in imitation of a natural tooth. On the other hand, the opposite side of the surface 10a on the oral cavity side of the dental prosthesis 10 is a surface 10c on the abutment side which is concaved. An abutment is inserted to the concaved portion to hold the dental prosthesis 10 in the oral cavity.

The dental prosthesis has a complicated shape and has a thinly-formed part. The material of the dental prosthesis has a large influence on quickly machining such a shape with a good accuracy without causing chippings and the like. In this embodiment, the lithium disilicate blank for a dental prosthesis and the dental prosthesis made from the blank are formed from a material for a dental prosthesis as described below.

That is, the material for a dental prosthesis is made including the following components. The main crystalline phase of the material is lithium disilicate.

$SiO_2$: no less than 60.0 mass % and no more than 80.0 mass %

$Li_2O$: no less than 10.0 mass % and no more than 20.0 mass %

$Al_2O_3$: no less than 5.1 mass % and no more than 10.0 mass %

If the components are not within the above ranges, there will be an increasing possibility of causing defects in the machinability.

In addition, if $SiO_2$ is not within the above range, it will be difficult to obtain a homogeneous glass blank. Preferably the range of $SiO_2$ is no less than 65 mass % and no more than 75 mass %. If $Li_2O$ is not within the above range either, it will be difficult to obtain a homogeneous glass blank. Preferably the range of $Li_2O$ is no less than 11 mass % and no more than 17 mass %. If $Al_2O_3$ is less than 5.1 mass %, it will cause problems in the machinability, even though lithium disilicate precipitates as the main crystalline phase. If $Al_2O_3$ is more than 10.0 mass %, lithium disilicate does not precipitate as the main crystalline phase (for example lithium aluminosilicate precipitates).

Further, the material for a dental prosthesis may include the following components, in addition to the above-mentioned components. However, as can be seen from the range of the components including 0 mass %, the components shown here are not necessarily included, and any one or more of them can be included.

$Na_2O$: no less than 0 mass % and no more than 2.8 mass %

$Rb_2O$: no less than 0 mass % and no more than 2.8 mass %

$Cs_2O$: no less than 0 mass % and no more than 2.8 mass %

$Fr_2O$: no less than 0 mass % and no more than 2.8 mass %

$K_2O$: no less than 0 mass % and no more than 10.0 mass %

$MgO$: no less than 0 mass % and no more than 3.0 mass %

$CaO$: no less than 0 mass % and no more than 3.0 mass %

$BeO$: no less than 0 mass % and no more than 3.0 mass %

$SrO$: no less than 0 mass % and no more than 10.0 mass %

$BaO$: no less than 0 mass % and no more than 10.0 mass %

$RaO$: no less than 0 mass % and no more than 10.0 mass %

By having these components, it is possible to adjust the melting temperature of materials in producing the material for a dental prosthesis. However, the improvement in the effect is limited even if the components are included more than the above ranges. Therefore, it is preferable that the components are included within the above ranges.

In addition, the following compounds to be materials for forming crystal nuclei can be included. The kind of the materials for forming crystal nuclei is not particularly limited, and known materials for forming crystal nuclei can be widely applied. This makes it possible to efficiently generate crystal nuclei which form lithium disilicate crystalline. Examples of the materials for forming crystal nuclei include $P_2O_5$, $ZrO_2$, $TiO_2$, $Ta_2O_5$, $ZnO$, $Nb_2O_5$, $Y_2O_3$, and $La_2O_3$. The materials as described above can be included within a range of no less than 0 mass % and no more than 10.0 mass %.

Further, the material for a dental prosthesis can include a known coloring agent, in order to resolve a feeling of strangeness in view of having aesthetics similar to a natural tooth. Examples of the coloring agent include $V_2O_5$, $CeO_2$, and $Er_2O_3$.

According to the material for a dental prosthesis, the lithium disilicate blank for a dental prosthesis, and a dental prosthesis produced by processing the blank, it is possible to provide strength, hardness, chemical durability against the intraoral environment, and aesthetics (color and texture) similar to a natural tooth, which are basic functions as a dental prosthesis. In addition, the machinability improves, therefore the lithium disilicate blank for a dental prosthesis can be machined by cutting and the like as it is, without requiring any post processing, for example, press molding, pulverizing the blank to form it into a powder thereafter forming a shape again, or heating the blank after processing. Therefore, even though the blank has sufficient strength, it can be machined under nearly same conditions as in processing conventional ceramic materials for cutting, without causing defects.

Here, preferably, a void is not observed in a microphotograph at a magnification of 2000 times on a cross section of the material for the dental prosthesis. However, since some voids are considered to have small influence, preferably, an area occupied by the voids in an observation range (for example 60 µm in length and 60 µm in width) is 2% or less.

Similarly, it is preferable that a granular material of a colorant is not observed in a microphotograph of the cut and polished surface of the dental prosthesis at a magnification of 200 times. More specifically, the particles of the colorant are not preferably observed within the observation range of 1 mm in length and 1 mm in width.

Next, one example of the method for producing the above-mentioned dental prosthesis will be explained. This includes a method for producing a lithium disilicate blank for a dental prosthesis, and a lithium disilicate blank for a dental prosthesis. The production method of this embodiment includes a melting step, a glass blank production step, a lithium disilicate blank production step (heating step), a cooling step, and a processing step.

The melting step is a step of mixing the materials described as the above-mentioned components and melting them at a temperature of no less than 1300° C. and no more than 1600° C. Whereby, a melt of a starting glass of the material for a dental prosthesis can be obtained. The melting is preferably carried out for several hours to make the melt sufficiently homogeneous.

The glass blank production step is a step of pouring the melt of a starting glass obtained in the melting step in a mold and cooling it to produce a glass blank. The temperature to cool the melt is preferably same as or lower than the glass transition temperature of the melt, and more preferably in between the room temperature and the glass transition temperature.

The lithium disilicate blank production step (heating step) is a step of heating the glass blank obtained in the glass blank production step, to obtain a lithium disilicate blank whose main crystalline phase is lithium disilicate. The lithium disilicate production step (heating step) includes a crystal nucleation step and a crystal growing step.

The crystal nucleation step is a step of heating the glass blank obtained in the glass blank production step and keeping it at a temperature of no less than 400° C. and no more than 600° C. for a predetermined time period. Whereby, crystal nuclei for generating crystal are formed. The keeping time is preferably 10 minutes or more so that the crystal nuclei are sufficiently formed. The upper limit of the keeping time is not particularly limited, and can be 6 hours or less.

The crystal growing step is a step of heating the glass blank without cooling it from the crystal nucleation step, and keeping it at a temperature of no less than 800° C. and no more than 1000° C. for a predetermined time period. Whereby, crystals of lithium disilicate grow and a lithium disilicate blank whose main crystalline phase is lithium disilicate can be obtained. The keeping time is preferably 1 minute or more, and more preferably 3 minutes or more. The upper limit of the keeping time is not particularly limited, and can be 3 hours or less.

The crystal growing step can be provided with an interval process which is carried out at a different temperature. That is, before the glass blank is kept at a temperature of no less than 800° C. and no more than 1000° C., heating the glass blank following to the crystal nucleation step, without cooling the glass blank, thereafter keeping it at a temperature of no less than 600° C. and no more than 800° C. for a predetermined time period. Whereby, an intermediate in which crystals are generated is obtained. The keeping time is preferably 10 minutes or more. The upper limit of the time is not particularly limited, and can be 6 hours or less. Alternatively, after the interval process, the blank can be heated to be kept at a temperature of no less than 800° C. and no more than 1000° C. as described above, without being cooled.

In the crystal nucleation step and the crystal growing step, the blank needs to be kept within a predetermined temperature range, as described above. However, as long as it is kept within a predetermined temperature range, the blank does not need to be kept at a certain temperature. That is, the temperature of the blank can be kept increased.

Here, the lithium disilicate blank is a blank (material) in which lithium disilicate is formed as the main crystalline phase. It is more preferable that the blank has a shape suitable for carrying out machining to a shape of a dental prosthesis. In particular, the suitable shape includes a block and disk for producing a dental prosthesis.

The cooling step is a step of cooling the lithium disilicate blank obtained in the lithium disilicate blank production step to a normal temperature. This makes it possible to provide the lithium disilicate blank to the processing step.

The processing step is a step of processing the obtained lithium disilicate blank to form it into a shape of a dental prosthesis by machining. The method of the machining is not particularly limited, and cutting, grinding and the like can be given. Whereby, a dental prosthesis is obtained. The effect is remarkably seen particularly in cutting work, for example chippings can be prevented.

This processing can be carried out under better conditions for productivity than before. That is, conventional materials for a dental prosthesis having lithium disilicate as their main crystalline phase cannot be efficiently cut, since they have poor machinability. Therefore, the conventional materials need to be processed in a state easy to be processed and of not having lithium disilicate as their main crystalline phase, thereafter have a process to increase strength, such as a heating treatment.

In contrast, according to the present invention, even though the material has lithium disilicate as the main crystalline phase, cutting and grinding can be carried out under similar conditions as in processing conventional materials easy to be processed. In addition, the present invention does not need a heating treatment after processing. Therefore it does not change the shape and a dental prosthesis can be made keeping the accuracy of machining. Further, there is no need to carry out press molding, pulverize and form again the material, and it is possible to machine the material as a block body, to directly form a final product.

EXAMPLES

With the above-described production method, lithium disilicate blanks whose main crystalline phases were lithium disilicate were prepared as Examples (No. 1 to No. 9) in which components included were different from one another. A dental prosthesis was produced from each of the blanks by cutting work, and the machinability and strength of the dental prosthesis when the prosthesis was produced were evaluated.

In Table 1, contents of each component are shown by mass %. Materials as Comparative Examples (No. 10 to No. 15) were also prepared and evaluated in the same way. In Table 1, components of main crystalline phase, machinability, and strength are shown as results. The blanks in the sections of components in Table 1 mean 0 mass %.

The "main crystalline phase" was measured by means of a multipurpose X-ray diffractometer Empyrean (PANalytical), which represented a crystal phase having the highest ratio as a result of a high-accuracy quantitative analysis by Rietveld method. In Table 1, "LS2" represents lithium disilicate and "LAS" represents lithium alminosilicate.

For the evaluation of machinability, two kinds of conventional materials for processing were prepared as References 1 and 2 shown below. Each of them was a material as follows.

(Reference 1) a material whose main crystalline phase is lithium metasilicate, including 72.3 mass % of $SiO_2$, 15.0 mass % of $Li_2O$, and 1.6 mass % of $Al_2O_3$.

(Reference 2) a material including crystalline phase of lithium metasilicate and crystalline phase of lithium disilicate with a nearly same ratio, including 56.3 mass % of $Si_2O$, 14.7 mass % of $Li_2O$, and 2.1 mass % of $Al_2O_3$.

Regarding Examples and Comparative Examples, each processing time, degree of tool wear, and degree of chippings compared to the materials of References 1 and 2 were evaluated. Materials same as or better than the References 1 and 2 in all of the processing time, degree of tool wear, and degree of chippings were rated as "good", and materials inferior to References 1 and 2 in any one or more of the processing time, degree of tool wear, and degree of chippings were rated as "inferior".

The "strength" was shown by the biaxial bending strength (MPa) calculated from a biaxial bending test for the lithium disilicate blanks according to ISO 6872. The strength of the material of Reference 1 was 370 MPa and the strength of the material of Reference 2 was 230 MPa.

TABLE 1

| | | Examples | | | | | | | | | Comparative Examples | | | | | |
|---|---|---|---|---|---|---|---|---|---|---|---|---|---|---|---|---|
| | | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 |
| Component | $SiO_2$ | 63.0 | 65.2 | 73.3 | 71.2 | 75.3 | 64.7 | 70.6 | 76.2 | 75.7 | 57.3 | 56.3 | 73.7 | 65.5 | 81.7 | 66.5 |
| | $Li_2O$ | 19.6 | 18.0 | 17.0 | 15.3 | 15.2 | 12.5 | 12.1 | 11.0 | 10.1 | 15.4 | 15.5 | 13.8 | 14.5 | 10.6 | 11.6 |
| | $Al_2O_3$ | 5.1 | 7.3 | 5.3 | 6.8 | 6.1 | 9.1 | 7.0 | 7.8 | 6.3 | 12.8 | 1.5 | 3.5 | 11.3 | 2.5 | 13.3 |
| | $Na_2O$ | | 0.3 | 0.5 | | | 2.6 | | 1.7 | 2.3 | | 1.0 | | 5.6 | 3.2 | 1.1 |
| | $K_2O$ | 2.7 | | 0.3 | 1.2 | 0.2 | 2.5 | 9.2 | | | 11.8 | 3.0 | | | 1.3 | 5.6 |
| | MgO | 2.1 | | 2.5 | | | | | | 0.3 | 0.2 | | | | 0.4 | |
| | CaO | | 2.8 | | | 1.2 | 0.4 | | | | | 0.5 | | | 3.4 | |
| | SrO | | 3.1 | 1.0 | | | 2.2 | | | | | 0.2 | | | | |
| | BaO | 1.3 | | | | | 0.9 | | | 5.1 | | | | 2.2 | | |
| | $P_2O_5$ | 4.1 | 1.5 | 0.1 | | 2.0 | 2.7 | 1.1 | | | 1.0 | 6.0 | 3.4 | 1.3 | | 0.8 |
| | $ZrO_2$ | 2.1 | 0.1 | | 5.4 | | | | 3.1 | 0.2 | 1.5 | 14.0 | | 1.6 | | 1.0 |
| | $TiO_2$ | | 1.7 | | 0.1 | | 2.4 | | 0.2 | | | 2.0 | | | 0.5 | 0.1 |
| Result | Main crystal | LS2 | LS2 | LS2 | LS2 | LS2 | LS2 | LS2 | LS2 | LS2 | LAS | LS2 | LS2 | LAS | LS2 | LAS |
| | Machinability | good | good | good | good | good | good | good | good | good | inferior | inferior | inferior | inferior | inferior | inferior |
| | Strength | 260 | 315 | 375 | 396 | 453 | 385 | 362 | 351 | 347 | 320 | 250 | 310 | 235 | 183 | 284 |

As can be seen from Table 1, according to the production of a dental prosthesis of Examples, it is possible to obtain good machinability and required strength, in addition to having lithium disilicate (LS2) as the main crystalline phase. In contrast, all of Comparative Examples were inferior in machinability, and some of them had low strength. In addition, in No. 10, 13, and 15 of Comparative Examples, lithium alminosilicate was generated and lithium disilicate was not formed as the main crystalline phase.

DESCRIPTION OF REFERENCE NUMERALS

10 dental prosthesis

The invention claimed is:

1. A block body before a dental prosthesis is produced therefrom by cutting work, the block body comprising:
a material comprising
$SiO_2$ in an amount of 60.0 mass % to 80.0 mass %,
$Li_2O$ in an amount of 10.0 mass % to 12.5 mass %,
$Al_2O_3$ in an amount of 5.1 mass % to 10.0 mass %, and
no $Ta_2O_5$,
wherein the block body is formed in a column, and a main crystalline phase is lithium disilicate.

2. The block body according to claim 1, the material further comprising:
at least one selected from the group consisting of $Na_2O$ in an amount of no more than 2.8 mass %, $K_2O$ in an amount of no more than 2.7 mass %, and $TiO_2$ in an amount of no more than 10.0 mass %.

3. The block body according to claim 1, the material further comprising:
at least one selected from the group consisting of CaO in an amount of no more than 3.0 mass %, SrO in an amount of no more than 10.0 mass %, BaO in an amount of no more than 10.0 mass %, MgO in an amount of no more than 3.0 mass %, $Rb_2O$ in an amount of no more than 2.8 mass %, Cs$_2$O in an amount of no more than 2.8 mass %, and BeO in an amount of no more than 3.0 mass %.

4. The block body according to claim 1, the material further comprising: ZrO$_2$ in an amount of no more than 10 mass %.

5. The block body according to claim 1, wherein machinability is the same as or better than those of first and second references, the machinability being compared in a processing time, a degree of tool wear, and chippings, the first reference being a material whose main crystalline phase is lithium metasilicate, the material comprising SiO$_2$ in an amount of 72.3 mass %, Li$_2$O in an amount of 15.0 mass %, Al$_2$O$_3$ in an amount of 1.6 mass %, the second reference being a material comprising a crystalline phase of lithium metasilicate and a crystalline phase of lithium disilicate with a same ratio, Si$_2$O in an amount of 56.3 mass %, Li$_2$O in an amount of 14.7 mass %, and Al$_2$O$_3$ in an amount of 2.1 mass %.

6. The block body according to claim 1, wherein in an observation range of 60 μm in length and 60 μm in width on a cross section of the block body, an area occupied by voids is less than 2%.

7. The block body according to claim 1, wherein particles of a colorant are not observed within an observation range of 1 mm in length and 1 mm in width on a cross section of the block body.

8. A lithium disilicate blank for a dental prosthesis to be machined into a shape of a dental prosthesis without press molding, the lithium disilicate blank comprising:
   SiO$_2$ in an amount of 60.0 mass % to 80.0 mass %;
   Li$_2$O in an amount of 10.0 mass % to 12.5 mass %;
   Al$_2$O$_3$ in an amount of 5.1 mass % to 10.0 mass %; and
   no Ta$_2$O$_5$
   wherein a main crystalline phase is lithium disilicate.

9. The lithium disilicate blank according to claim 8, further comprising:
   at least one of ZrO$_2$ in an amount of 0.1 mass % to 10.0 mass %, and K$_2$O in an amount of 0.2 mass % to 10 mass %.

10. A lithium disilicate blank for a dental prosthesis to be machined into a shape of a dental prosthesis to form a dental prosthesis without a heating treatment after the machining, the lithium disilicate blank comprising:
    SiO$_2$ in an amount of 60.0 mass % to 80.0 mass %;
    Li$_2$O in an amount of 10.0 mass % to 12.5 mass %;
    Al$_2$O$_3$ in an amount of 5.1 mass % to 10.0 mass %, and
    no Ta$_2$O$_5$
    wherein a main crystalline phase is lithium disilicate.

11. The lithium disilicate blank according to claim 10, further comprising:
    at least one of ZrO$_2$ in an amount of 0.1 mass % to 10.0 mass %, and K$_2$O in an amount of 0.2 mass % to 10 mass %.

* * * * *